(12) United States Patent
Busacca et al.

(10) Patent No.: US 7,491,851 B2
(45) Date of Patent: *Feb. 17, 2009

(54) METHOD FOR GENERATING SECONDARY PHOSPHINES

(75) Inventors: Carl Alan Busacca, Poughkeepsie, NY (US); Jon C. Lorenz, New Milford, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/675,851

(22) Filed: Feb. 16, 2007

(65) Prior Publication Data

US 2007/0149820 A1 Jun. 28, 2007

Related U.S. Application Data

(63) Continuation of application No. 11/034,089, filed on Jan. 12, 2005, now Pat. No. 7,256,314.

(60) Provisional application No. 60/536,203, filed on Jan. 13, 2004.

(51) Int. Cl.
*C07F 9/02* (2006.01)

(52) U.S. Cl. .................. 568/17; 568/8; 568/9

(58) Field of Classification Search ............ 568/8, 568/9, 17

See application file for complete search history.

(56) References Cited

U.S. PATENT DOCUMENTS 4,113,783 A * 9/1978 Malpass et al. .......... 568/17
5,648,549 A * 7/1997 Kleiner ................. 568/17

OTHER PUBLICATIONS

Million et al., The Mechanism of the Reduction of Diphenylphosphinic acid and its Ethyl Ester by Lithium Aluminum halide, J. Chem. Soc., Suppl. (1964) 6121-6130.*
Senda, T., et al. Rhodium-Catalyzed Asymmetric 1, 4 Addition of Organoboron Reagents to 5, 6-Dihydro-2(1H)-pyridinones, Asymmetric Synthesis of 4 Aryl-2 piperidinones, J. Org. Chem. 2001, 66, 6852-6856, XP-002977097.
Kapoor, P.N., et al; Synthesis of Three New Ditertiary Phosphines: 1-Diphenylophospino-2-BIS(m-Fluorophenyl) Phosphinoethane, 1 Diphenylphosphino-2-BIS(p-Fluorophenyl) Phosphinoethane and 1 Diphenylphosphino-2-m BIS Journal of Organometallic Chemistry (1984), 276 (2) 167-170.
(Trifluoromethyl)Phenyl-phosphinoethane: Journal of Organometallic Chemistry, 276 (1984) 167-170 XP 002327624.
McKinstry, L., et al.: On the Asymmetric Rh(1) Catalyzed [4+2] Cycloisomerization Reaction. Electronic and Torsional Ligand Control of Absolute Stereoselection. Tetrahedron vol. 50, No. 21, pp. 6145-6154, 1994 XP-002327625.

* cited by examiner

*Primary Examiner*—Daniel M Sullivan
*Assistant Examiner*—Chukwuma O Nwaonicha
(74) *Attorney, Agent, or Firm*—Michael P. Morris; Mary-Ellen M. Devlin; David L. Kershner

(57) ABSTRACT

This invention provides a method for generating secondary phosphines from secondary phosphine oxides in the presence of a reducing agent, such as diisobutylaluminum hydride (DIBAL-H), triisobutyldialuminoxane, triisobutylaluminum, tetraisobutyldialuminoxane, or another reducing agent comprising: (i) an $R_1R_2AlH$ moiety, wherein $R_1$ and $R_2$ are each an alkyl species or oxygen, and wherein at least one of $R_1$ or $R_2$ comprises at least 2 carbon atoms, or (ii) an $R_1R_2R_3Al$ moiety, wherein $R_1$, $R_2$, and $R_3$ are not hydrogen, and wherein at least one of $R_1$, $R_2$, and $R_3$ is an alkyl species comprising a β-hydrogen, not including triethylaluminum. Preferred reducing agents for the present invention include: diisobutylaluminum hydride, triisobutyldialuminoxane, triisobutylaluminum, tetraisobutyldialuminoxane, and combinations thereof.

10 Claims, No Drawings

METHOD FOR GENERATING SECONDARY PHOSPHINES

CROSS-REFERENCE TO RELATED APPLICATIONS

This application claims the benefit of U.S. Provisional Patent Application No. 60/536,203 filed Jan. 13, 2004 and U.S. patent application Ser. No. 11/034,089 filed Jan. 12, 2005, the entireties of which are incorporated herein by reference.

FIELD OF INVENTION

This invention relates to organic compounds and methods for their preparation. More specifically, this invention relates to an improved method for the production of secondary phosphines using a reducing agent comprising a tri-coordinate aluminum moiety. In particular, this invention relates to a method for the reduction of secondary phosphine oxides to secondary phosphines using a reducing agent comprising a tri-coordinate aluminum moiety.

BACKGROUND OF THE INVENTION

Most ligands for asymmetric catalysis contain phosphines, including the phosphinoimidazolines found, for example, in U.S. Pat. No. 6,316,620. A common method for construction of these phosphine ligands involves coupling with a secondary phosphine, $R_2PH$.

A fundamental physical property of secondary phosphines is their extreme air sensitivity. Most secondary phosphines will completely oxidize in air within a few minutes to typically undesired secondary phosphine oxides. Because of this problem, there is a long-felt need for improved synthetic procedures for the preparation of secondary phosphines employing a minimum number of synthetic steps and that minimize physical manipulations that may increase the possibility of contact with air.

Unfortunately, the prior art methods for preparation of these species suffer from numerous deficiencies.

One prior art method for the preparation of secondary phosphines, which has been proposed to reduce inadvertent oxidation, employs $BH_3$ complexes (Stankevič, M.; Pietrusiewicz, K. M. Synlett 2003, 7, 1012-1016). Unfortunately, in practice, this method has been found to generate undesirable byproducts. Further, there are severe hazards associated with handling $BH_3$ (Reisch, M. Chem. Eng. News 2002, 80(26), 7).

Another method available for producing secondary phosphines employs lithium aluminum hydride (LAH) (Kapoor, P. N.; Venanzi L. M. Helv. Chim. Acta 1977, 60(277), 2824-2829). The problem with LAH is that it is also a very hazardous substance to handle. Moreover, in practice, LAH has not been found useful for producing those phosphine ligands that are of particular interest in the art, such as the phosphinoimidazolines.

The reduction of secondary phosphine oxides to secondary phosphines has been accomplished with diphenylsilane (McKinstry, L.; Livinghouse T. Tetrahedron 1994, 50(21), 6145-6154). Unfortunately, this method requires very high temperatures (i.e., greater than 200° C.). Another method of reducing secondary phosphine oxides uses a combination of trichlorosilane ($Cl_3SiH$) and triethylamine (Elding, L. I.; Kellenberger, B.; Venanzi, L. M. Helv. Chim. Acta 1983, 66(6), 1676). However, a significant problem with this method is that trichlorosilane is a corrosive reagent, whose extremely low boiling point (31° C.) and low flash point (−13° C.) make it completely unsuitable for typical plant operations.

One of the most common methods for synthesis of secondary phosphine oxides used in industry is a two step process in which an intermediate secondary chlorophosphine is produced (Casalnuovo, A. L; RajanBabu T. V.; Ayers, T. A.; Warren, T. H. J. Am. Chem. Soc. 1994, 116(22), 9869). A chlorophosphine, an air-sensitive and water-sensitive compound, is first prepared and then isolated. This is carried out with phosphorous trichloride ($PCl_3$), which is a corrosive reagent. High vacuum is employed to fully remove the by-products of this reaction. The chlorophosphine must then be reduced, usually, by LAH, with the hazards associated with using that reagent.

Therefore, there is a need for an improved method for generating secondary phosphines in high yield and purity, without the need to employ hazardous materials.

In U.S. Pat. No. 4,113,783 to Malpass et al., which corresponds to Great Britain Patent No. 1,520,237 to Texas Alkyls, there is described the use of DIBAL-H for the reduction of a tertiary phosphine oxide, triphenylphosphine oxide, to a tertiary phosphine, triphenylphosphine. The patent is specifically directed to triphenylphosphine oxide. No other tertiary phosphine oxides are cited. There is no suggestion for application of DIBAL-H with respect to the reduction of secondary phosphine oxides. Therefore, the usefulness of DIBAL-H in the reduction of secondary phosphine by the present inventor was entirely unexpected.

SUMMARY OF THE INVENTION

This invention provides a method for generating secondary phosphines from secondary phosphine oxides in the presence of a reducing agent, such as diisobutylaluminum hydride (DIBAL-H), triisobutyldialuminoxane, triisobutylaluminum, tetraisobutyldialuminoxane, or another reducing agent comprising: (i) an $R_1R_2AlH$ moiety, wherein $R_1$ and $R_2$ are each an alkyl species or oxygen, and wherein at least one of $R_1$ or $R_2$ comprises at least 2 carbon atoms, or (ii) an $R_1R_2R_3Al$ moiety, wherein $R_1$, $R_2$, and $R_3$ are not hydrogen, and wherein at least one of $R_1$, $R_2$, and $R_3$ is an alkyl species comprising a β-hydrogen, not including triethylaluminum.

Preferred reducing agents for the present invention include: diisobutylaluminum hydride, triisobutyldialuminoxane, triisobutylaluminum, tetraisobutyldialuminoxane, and combinations thereof.

DETAILED DESCRIPTION OF THE INVENTION

The preferred solution to the aforementioned problems of spontaneous oxidation and accompanying hazards in the production of phosphine ligands is to use an alkyl-substituted, tri-coordinate aluminum species, such as diisobutylaluminum hydride (DIBAL-H), in order to reduce secondary phosphine oxides to secondary phosphines. The alkyl-substituted, tri-coordinate aluminum species of the present invention are referred to herein as "reducing agents." Traditionally defined, a reducing agent according to the present invention donates electrons to the secondary phosphine oxide, such that the oxygen is removed therefrom. Nonetheless, it is surprisingly notable that a preferred reducing agent of the present invention, i.e., DIBAL-H, is also traditionally defined as a Lewis acid. Moreover, the reducing agents of the present invention are also referred to herein as "organometallic." Compounds that are organometallic comprise a metal-carbon bond.

The organometallic reducing agents according to the present invention may be dialkyl species (i.e., two alkyl groups bonded with the metal atom) or trialkyl species (i.e., three alkyl groups bonded with the metal atom). As used herein, "alkyl" refers to groups comprising branched or unbranched hydrocarbons, which may be unsubstituted or substituted. Dialkyl species are more preferred in comparison to trialkyl species.

Whether a particular organometallic reducing agent according to the present invention is a dialkyl or trialkyl species, at least one alkyl group thereof must comprise at least 2 carbon atoms. In light of this attribute of the reducing agents, while not being limited to a particular reaction mechanism, it is believed that a β-hydride elimination event occurs in reduction reactions created by reducing agents of the present invention that do not comprise an aluminum hydride (AlH) moiety. For those reducing agents that do comprise an aluminum hydride moiety, it is possible that the reduction reaction will go to completion without a β-hydride elimination event, especially when the reduction reaction uses an excess of the AlH-containing reducing agent. Triethylaluminum is explicitly excluded from the present invention because it is not a reducing agent (Zhurnal Obshchei Khimii 1992, 62(5), 1027).

Therefore, the present invention is directed to a reducing agent comprising: (i) an $R_1R_2AlH$ moiety, wherein $R_1$ and $R_2$ are each an alkyl species or oxygen, and wherein at least one of $R_1$ or $R_2$ comprises at least 2 carbon atoms, and/or (ii) $R_1R_2R_3Al$ moiety, wherein $R_1$, $R_2$, and $R_3$ are not hydrogen, and wherein at least one of $R_1$, $R_2$, and $R_3$ is an alkyl species comprising a β-hydrogen, not including triethylaluminum.

Examples of dialkyl aluminum species contemplated by the present invention include: diethylaluminum chloride, diisobutylaluminum chloride, disecbutylaluminum choride, diethylaluminum hydride, diisobutylaluminum hydride, and disecbutylaluminum hydride, and triisobutylaluminoxane.

Dialkyl species of the organometallic reducing agents of the present invention may comprise any suitable ion, such as a chloride or hydride ion. A preferred dialkyl species for the organometallic reducing agents of the present invention comprises a hydride ion.

Examples of trialkyl aluminum species contemplated by the present invention include: tri-n-butylaluminum, tri-iso-butylaluminum, tri-sec-butylaluminum, trihexylaluminum, tri-n-octylaluminum, Further suitable aluminum species for use in the present invention include higher molecular weight trialkylaluminums, i.e., substituted with $C_2$-$C_{20}$ alkyl groups, such as trioctylaluminum, trioctadecylaluminum, and tridocosylaluminum.

DIBAL-H, a preferred reducing agent according to the present invention, is a very robust and safe reducing agent that has been used extensively in plant operations. It is not a hazardous reducing agent like LAH or borane. It is inexpensive, and can be purchased commercially in bulk in neat form. DIBAL-H may be dispensed in process-safe solvents, such as tetrahydrofuran (THF), toluene, and heptane, which do not have the low boiling point and flash point problems associated with $Cl_3SiH$. Unexpectedly, it has been found that DIBAL-H reduction of secondary phosphine oxides may be effectuated between ambient temperature (e.g., room temperature) and the reflux temperature of THF (67° C.), particularly when the secondary phosphine oxide does not comprise electron withdrawing substituents. Therefore, high temperatures, such as those required for phenylsilane, are not needed with the DIBAL-H reduction method of the present invention. Alternatively, particularly when the secondary phosphine oxide does comprise electron withdrawing substituents, the reduction may be effectuated below ambient temperature.

As compared to a commonly used prior art process for reducing secondary phosphine oxides using LAH, wherein a 1:1 mixture of the desired secondary phosphine is formed with the unwanted primary phosphine, reduction with a reducing agent of the present invention (e.g., DIBAL-H) causes no primary phosphine to be formed as illustrated below.

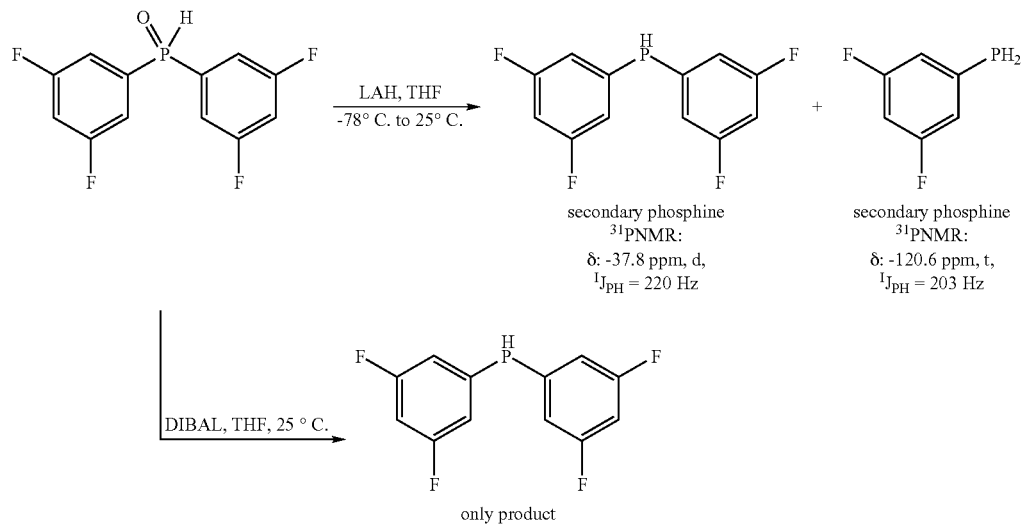

As exemplified by reference to DIBAL-H, reduction reactions of the present invention creates a more pure product in a single reaction step. This is also evident when reduction reactions using organometallic reducing agents of the present invention, e.g., DIBAL-H, are compared to reduction reactions using borane, wherein the latter method forms significant amounts of unwanted hydroxyphosphines.

Since secondary phosphines are known to be extremely air-sensitive, most conventional purification methods cannot be used. Distillation is the purification method used in the art. Many substituted secondary phosphines have extremely high boiling points—in fact, many are solids at ambient temperature. The high boiling points and the difficulties associated with achieving very high vacuum in a plant setting combine to make purification by distillation very difficult if not impossible to apply productively and safely. The present method provides secondary phosphines of high purity so that further purification is unnecessary.

One embodiment of the invention provides a substantially anaerobic environment for the production of secondary phosphine comprising a reaction of a secondary phosphine oxide or mixture thereof with a DIBAL-H/solvent mixture, followed by neutralization and filtration of the product-containing organic phase to yield a phosphine product of high purity. An advantageous reflux process may comprise a temperature range from ambient temperature, such as room temperature, to a temperature not exceeding the solvent boiling point. Another embodiment of the invention provides a method comprising the steps of adding a secondary phosphine oxide to a pre-heated DIBAL-H and tetrahydrofuran mixture under inert, anaerobic gas pressure, refluxing the reaction mixture to completion, cooling the same to a suitable (e.g., ambient or slightly below ambient) temperature, and quenching the same by neutralization with an aqueous hydroxide reagent. In yet another embodiment of the invention, neat DIBAL-H without an organic solvent is combined with the secondary phosphine oxide.

Non-limiting examples of the present reduction method for making secondary phosphines by employment of DIBAL-H, triisobutyldialuminoxane, triisobutylaluminum, and tetraisobutyldialuminoxane is set forth below.

EXAMPLE 1

Production of Bis-(3-fluorophenyl) Phosphine by Reduction with DIBAL-H

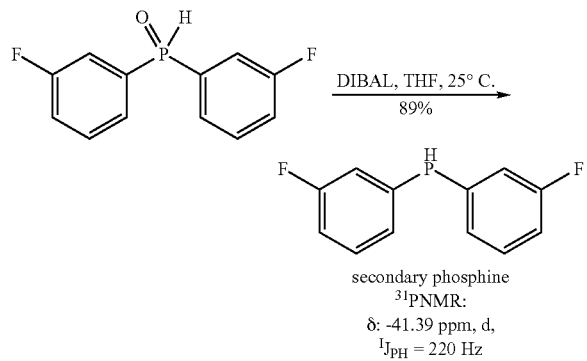

secondary phosphine
$^{31}$PNMR:
δ: -41.39 ppm, d,
$^{1}J_{PH}$ = 220 Hz

A 2-neck 100 mL flask with a Vigreux condenser was evacuated/Ar filled (3×), then charged with 6.00 mL 1M DIBAL-H/THF (6.00 mmol, 3 eq.), then heated to 65° C. under $N_2$. To the warm solution, 476 mg bis (3-fluorophenyl)-phosphine oxide (2.00 mmol, 1 eq.) in 4.0 mL THF was added in drops from a syringe over 15 minutes, with caution taken for gas evolution. After one hour at reflux, TLC of a quenched aliquot showed the reaction was complete to a non-polar product. The mixture was cooled to ambient temperature, and then cautiously quenched by the slow addition of 10 mL 5% aqueous NaOH. The mixture was stirred vigorously for 10 minutes, then 10 mL of 1:1 MTBE:Hexane was added, and the mixture was again stirred vigorously for 10 minutes. After stirring was stopped, the phases were allowed to separate, and the upper organic phase was transferred, via canula, under $N_2$ pressure, to an air-free filter funnel containing $MgSO_4$, which was attached directly to a 2-neck pear shaped flask as receiver. When the filtration was complete, an $N_2$ line was inserted in the side neck of the pear flask, and the solvents were removed by evaporation over one hour. The product collected in the base of the pear flask: 400 mg (89%), as a colorless oil. $^{31}$P NMR showed the desired secondary phosphine. $^{31}$P NMR ($CDCl_3$, 162 MHz): δ=-41.39 ppm, d, $^{1}J_{PH}$=220 Hz.

EXAMPLE 2

Production of Pheylisopropyl Phosphine by Reduction with Triisobutyidialuminoxane A flask was charged with 2.0 mL 0.36M triisobutyldialuminoxane/toluene solution (0.72 mmol, 2 eq.), then cooled to -78° C. under Ar. To this cold solution was then added a solution of 60 mg phenylisopropylphosphine oxide (0.36 mmol, 1 eq.) in 0.75 mL $^{8}$d THF. Gas evolution was observed. The flask was then allowed to warm to 25° C. After 2 h at 25° C., $^{31}$P NMR of an aliquot showed the reaction was already 50% complete to the desired secondary phosphine, phenylisopropyl phosphine, with $^{31}$P NMR δ=-27.4 ppm.

EXAMPLE 3

Production of Pheylisopropyl Phosphine by Reduction with Triisobutylaluminum

A screw-cap NMR tube was charged with 0.50 mL 1M i-$Bu_3$Al/Hexane solution (0.50 mmol, 1 eq.), then cooled to -78° C. under Ar. To this cold solution was then added a solution of 84 mg Phenylisopropylphosphine oxide (0.50 mmol, 1 eq.) in 0.15 mL $^{8}$d THF. Gas evolution was observed. The tube was then allowed to warm to 25° C. After only 15 min. at 25° C., $^{31}$P NMR showed the reaction was already 70% complete to the desired secondary phosphine, phenylisopropyl phosphine, with $^{31}$P NMR δ=-27.4 ppm.

EXAMPLE 4

Production of Pheylisopropyl Phosphine by Reduction with Tetraisobutyidialuminoxane A screw-cap NMR tube was charged with 0.50 mL 0.29M tetraisobutyl-dialuminoxane/toluene solution (0.145 mmol, 1 eq.). To this solution was then added a solution of 24.4 mg phenylisopropylphosphine oxide (0.145 mmol, 1 eq.) in 0.25 mL $^{8}$d THF. A small amount of gas evolution was observed. After only 1 hour at 25° C., 31P NMR showed the major product present was the desired secondary phosphine, Phenylisopropyl phosphine, with $^{31}$P NMR δ=-27.4 ppm.

EXAMPLE 5

Production of Other Secondary Phosphines by Reduction with DIBAL-H

Similar to the method of Example 1, a large number of secondary phosphine compounds were obtained by conversion from secondary phosphine oxides. (See Table 1).

The reductions in Table 1 are in THF with 3 equivalents of DIBAL-H unless otherwise noted.

TABLE 1

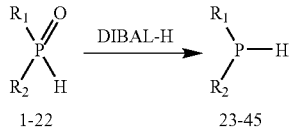

| $R_1$ | $R_2$ | Time (min.)/ Temp. (° C.) | Yield (%) | $^{31}$P NMR |
|---|---|---|---|---|
| $C_6H_5$ | $C_6H_5$ | 10/25 | 88 | $\delta = 44.35, J_{PH} = 218$ Hz |
| 4-F—$C_6H_4$ | 4-F—$C_6H_4$ | 10/25 | 90 | $\delta = -44.30, J_{PH} = 216$ Hz |
| 4-Cl—$C_6H_4$ | 4-Cl—$C_6H_4$ | 10/25 or 180/−25 | 83 | $\delta = -45.63, J_{PH} = 219$ Hz |
| 4-$CF_3$—$C_6H_4$ | 4-$CF_3$—$C_6H_4$ | 180/−78 | 79 | $\delta = -41.35, J_{PH} = 221$ Hz |
| 4-Me—$C_6H_4$ | 4-Me—$C_6H_4$ | 10/25 | 83 | $\delta = -44.66, J_{PH} = 214$ Hz |
| 3-F—$C_6H_4$ | 3-F—$C_6H_4$ | 60/−20 | 89 | $\delta = -41.39, J_{PH} = 220$ Hz |
| 3-Cl—$C_6H_4$ | 3-Cl—$C_6H_4$ | 60/−20 | 81 | $\delta = -40.29, J_{PH} = 219$ Hz |
| 3-F, 5-Me—$C_6H_3$ | 3-F, 5-Me—$C_6H_3$ | 60/−20 | 82 | $\delta = -39.66, J_{PH} = 219$ Hz |
| 3,5-$F_2$, 4-OMe—$C_6H_2$ | 3,5-$F_2$, 4-OMe—$C_6H_2$ | 60/−20 | 90 | $\delta = -40.03, J_{PH} = 220$ Hz |
| 3,5-$Cl_2$—$C_6H_3$ | 3,5-$Cl_2$—$C_6H_3$ | 60/−20 or 180/−25 | 90 | $\delta = -39.23, J_{PH} = 221$ Hz |
| 3,5-$F_2$—$C_6H_3$ | 3,5-$F_2$—$C_6H_3$ | 60/−20 or 180/−25 | 80 | $\delta = -37.80, J_{PH} = 220$ Hz |
| 3,5-$(CF_3)_2$—$C_6H_3$ | 3,5-$(CF_3)_2$—$C_6H_3$ | 60/−20 | 72 | $\delta = -41.06, J_{PH} = 224$ Hz |
| 4-OMe—$C_6H_4$ | 4-OMe—$C_6H_4$ | 10/25 | 91 | $\delta = -43.94, J_{PH} = 214$ Hz |
| 4-$NMe_2$—$C_6H_4$ | 4-$NMe_2$—$C_6H_4$ | 10/25 | 92 | $\delta = -45.82, J_{PH} = 211$ Hz |
| 2,4,6-$Me_3$—$C_6H_2$ | 2,4,6-$Me_3$—$C_6H_2$ | 180/25 | 30 | $\delta = -96.23, J_{PH} = 230$ Hz |
| 2-Naph | 2-Naph | 10/25 | 84 | $\delta = -39.96, J_{PH} = 216$ Hz |
| 3,5-$Me_2$—$C_6H_3$ | 3,5-$Me_2$—$C_6H_3$ | 60/25 | 90 | $\delta = -39.84, J_{PH} = 214$ Hz |
| Ph | $C_6H_{11}$ | 240/50 | 93 | $\delta = -30.4, J_{PH} = 206$ Hz |
| $C_6H_5$ | i-Pr | 10/25 | 90 | $\delta = -27.71, J_{PH} = 200$ Hz |
| $C_6H_5$ | t-Bu | 240/50 | 86 | $\delta = -8.1, J_{PH} = 227$ Hz |
| n-Bu | n-Bu | 60/25 | 85 | $\delta = -71.34, J_{PH} = 190$ Hz |
| $C_6H_{11}$ | $C_6H_{11}$ | 240/50 | 88 | $\delta = -27.93, J_{PH} = 191$ Hz |
| t-Bu | t-Bu | 240/50 | 87 | $\delta = -20.01, J_{PH} = 198$ Hz |

Preferably, the molar ratio of the tri-coordinate aluminum moiety, i.e., $R_1R_2AlH$ or $R_1R_2R_3Al$, to the secondary phosphine oxide is about 1:3 to about 10:1. Ideally, in reference to the molar ration of 1:3, a reducing agent having a single, tri-alkyl aluminum moiety comprising three β-hydrogen atoms, e.g., trialkylaluminum, may be able to reduce three secondary phosphine oxides. Practically, the molar ratio could be closer to 10:1. It may be preferable to provide an excess of reducing agent to better ensure that the reduction of the secondary phosphine oxides goes to completion.

Many suitable reducing agents for the present invention are liquid within a temperature range that is useful for effectuating a reaction with secondary phosphine oxides. When a given reducing agent is liquid at the desired reaction temperature, the given reducing agent may be used neat, i.e., without a solvent.

Alternatively, the reducing agent may be in a mixture with a solvent. The solvent may be selected from hydrocarbons, ethers, and halocarbons. For example, the solvent may be selected from the group consisting of: tetrahydrofuran, toluene, dioxane, xylene, hexane, heptane, cyclohexane, and other hydrocarbons, diethyl ether, and other dialkyl ethers, dichloromethane, dichloroethane, 2-methyl-THF, MTBE, monoglyme, diglyme, triglyme, tetraglyme, chloroform, methylcyclohexane, octane, di-n-butylether, diisopropylether, ethylbenzene, cyclopentylmethylether, and combinations and mixtures thereof. The secondary phosphine product may be isolated by any suitable means, such as by purification by partition separation from a mixture of an aqueous and an organic solvent. Likewise, the secondary phosphine product may be de-watered or dried by any suitable means, such as by distillation of an aqueous solvent. In a preferred embodiment the reduction reaction may be carried out anaerobically, for example, by replacing air with inert gas, such as argon and/or nitrogen. When a solvent is preset, the aluminum hydride-solvent mixture comprises a molar ration ranging from 1:20 to 20:1.

A significant advantage of the present invention is that the step of reacting the secondary phosphine with the reducing agent may be effectuated in a broad temperature range. Using the reducing agent and method of the present invention, it is possible to effectuate quick reduction reactions by using a high average temperature, controlled reduction reactions by using a low average temperature, or balanced reduction reactions by using an intermediate average temperature. Given the appropriate amount of time, intermediate or low average temperature is preferred. For the present invention, a high average temperature is an average temperature above about 50° C., a low average temperature is an average temperature below about −25° C., and an intermediate average temperature is a temperature between about −25° C. and about 50° C. Depending on the specific way in which the temperature of a particular reaction fluctuates over time, "average temperature" may be the mean temperature or the median temperature. For example, if a particular reduction reaction included a very brief, very large temperature deviation, but was very temperature stable otherwise, the average temperature for the particular reduction reaction may, more accurately, be defined as the median temperature, instead of the mean temperature, which would be inaccurately skewed.

For very electron-deficient secondary phosphine oxides, such as a tetrafluoro derivative, the reduction may be advantageously carried out at a low average temperature. In the absence of electron-withdrawing groups, a high average temperature may be required to effect the reduction. The method may be less efficient with very electron-rich phosphine oxides. In determining optimal reaction temperatures, an evaluation of the electronic nature of the secondary phosphine oxide should be taken into account.

In light of the fact that excess reducing agent is preferably used to better ensure complete reduction of the secondary phosphine oxide, a quenching agent is preferable used to neutralize any un-reacted reducing agent after the reduction reaction is finished. When used, the quenching agent is preferably an aqueous base in a concentration range approximately from about 10% to about 25%. The concentration of an aqueous base used for the quench could range approximately from 1%-50%. However, a value in the middle of this range is likely to be more productive, as, on the one hand, lower concentrations of this aqueous quencher may lead to more insoluble aluminum salts, while, on the other hand, higher concentrations may lead to product decomposition. A low concentration of the aqueous base may be used, as described in Example 1 hereinabove, wherein the concentration of the aqueous base NaOH was 5%. A high concentration of the aqueous base may also be used. A practical upper limited for the concentration of aqueous base is about 50%.

Moreover, the invention may also be practiced by quenching with a minimal amount of water rather than the excess water described in Example 1. However, this modification may generate insoluble materials, which are more difficult to separate from the product. It has been found that quenching DIBAL-H generates aluminum salts that are more soluble at basic pH than at neutral pH.

Preferably, the secondary phosphine is isolated from any water and/or aqueous reaction component. For example, after quenching with an aqueous base, the reaction mixture may be allowed to separate into an organic phase and an aqueous phase, which may be subsequently removed by any suitable means, such as drawing off the aqueous phase or evaporating the water. As would be understood by one of ordinary skill in the art, rather than removing the upper organic phase as described in Example 1, the lower aqueous phase may first be dropped to a second vessel (and re-extracted with an organic solvent, if necessary), and the original organic phase dropped to a third vessel for product isolation. If a chlorinated solvent such as dichloromethane ($CH_2Cl_2$) were used in the separation, the denser organic phase would be on the bottom, and the aqueous phase on the top. In this scheme, it may be advantageous to drop the lower organic phase through the bottom valve to a second vessel, and then (if desired) re-extract the remaining aqueous phase with $CH_2Cl_2$ to recover more product.

Furthermore, the organic solution containing the secondary phosphine may optionally be passed through a drying agent in an air-free filter. One may also use drying agents, such as sodium sulfate ($Na_2SO_4$), molecular sieves, silica gel, alumina, and the like. Silica gel and alumina may have an added benefit in that any polar impurities in the crude product solution would be removed in this manner.

When neutralized by a quenching agent, the reducing agent becomes aluminum by-product, which may be separated from the secondary phosphine. Separating aluminum by-product from the secondary phosphine may be considered separately from separating water from the secondary phosphine. For example, if the water is separated by evaporation/distillation, the aluminum by-product initially present in the aqueous phase may become a precipitate, which may be filtered from the organic phase containing the secondary phosphine.

After the water and aluminum by-product have been removed, the secondary phosphine may be isolated from the organic phase by any suitable means. Alternatively, it is possible to leave the secondary phosphine is the organic phase and/or with the aluminum by-product. If the secondary phosphine is not separated from the organic phase and/or the aluminum by-product, it is, nonetheless, most practical to isolate the secondary phosphine from water.

Although the inventive method is described in the context of synthesis of certain ligands as would be understood by the skilled artisan reading this disclosure, a large number of ligands formed by coupling with secondary phosphines may be synthesized.

What is claimed is:

1. A method for generating a secondary phosphine from a secondary phosphine oxide comprising a reaction of the secondary phosphine oxide and a reducing agent comprising an $R_1R_2AlH$ moiety, wherein $R_1$ and $R_2$ are each an alkyl species or oxygen, and wherein at least one of $R_1$ or $R_2$ comprises at least 2 carbon atoms.

2. The method of claim 1, wherein the reducing agent is selected from the group consisting of: diisobutylaluminum hydride, triisobutyldialuminoxane, and a combination thereof.

3. The method of claim 1, wherein the molar ratio of the $R_1R_2AlH$ moiety to the secondary phosphine oxide is about 1:3 to about 10:1.

4. The method of claim 1, the step of reacting the secondary phosphine oxide with the reducing agent does not generate a primary phosphine as a final product.

5. A method for generating a secondary phosphine from a secondary phosphine oxide comprising the step of reacting the secondary phosphine oxide with a reducing agent comprising an $R_1R_2R_3Al$ moiety, wherein $R_1$, $R_2$, and $R_3$ are not hydrogen, and wherein at least one of $R_1$, $R_2$, and $R_3$ is an alkyl species comprising a β-hydrogen atom, not including triethylaluminum.

6. The method of claim 5, wherein the reducing agent is selected from the group consisting of: triisobutylaluminum, tetraisobutyldialuminoxane, and a combination thereof.

7. The method of claim 5, wherein the molar ratio of the $R_1R_2R_3Al$ moiety to the secondary phosphine oxide is about 1:3 to about 10:1.

8. The method of claim 5, the step of reacting the secondary phosphine oxide with the reducing agent does not generate a primary phosphine as a final product.

9. The method in accordance with claim 1 wherein the reaction of the secondary phosphine oxide and a reducing agent is effectuated at a temperature of less than 140° C.

10. The method in accordance with claim 5 wherein the reaction of the secondary phosphine oxide and a reducing agent is effectuated at a temperature of less than 140° C.

* * * * *